(12) United States Patent
Bedoukian

(10) Patent No.: US 9,512,059 B2
(45) Date of Patent: *Dec. 6, 2016

(54) KILLING OF BED BUGS

(71) Applicant: BEDOUKIAN RESEARCH, INC., Danbury, CT (US)

(72) Inventor: Robert H. Bedoukian, West Redding, CT (US)

(73) Assignee: Bedoukian Research, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/391,305

(22) PCT Filed: Apr. 30, 2013

(86) PCT No.: PCT/US2013/000119
§ 371 (c)(1),
(2) Date: Oct. 8, 2014

(87) PCT Pub. No.: WO2013/165475
PCT Pub. Date: Nov. 7, 2013

(65) Prior Publication Data
US 2015/0087855 A1    Mar. 26, 2015

Related U.S. Application Data

(60) Provisional application No. 61/687,921, filed on May 2, 2012.

(51) Int. Cl.
| | |
|---|---|
| *C07C 69/00* | (2006.01) |
| *C07C 69/533* | (2006.01) |
| *A01N 35/06* | (2006.01) |
| *A01N 31/06* | (2006.01) |
| *A01N 37/02* | (2006.01) |
| *A01N 35/02* | (2006.01) |
| *C07C 35/18* | (2006.01) |
| *C07C 49/543* | (2006.01) |

(52) U.S. Cl.
CPC ............ *C07C 69/533* (2013.01); *A01N 31/06* (2013.01); *A01N 35/02* (2013.01); *A01N 35/06* (2013.01); *A01N 37/02* (2013.01); *C07C 35/18* (2013.01); *C07C 49/543* (2013.01)

(58) Field of Classification Search
CPC ...... A01N 31/06; A01N 35/02; A01N 35/06; A01N 37/02; C07C 35/18; C07C 49/543; C07C 69/533
See application file for complete search history.

(56) References Cited

U.S. PATENT DOCUMENTS

| | | | |
|---|---|---|---|
| 4,332,941 A | 6/1982 | Berthold et al. | |
| 7,579,016 B2 | 8/2009 | Zhang et al. | |
| 8,142,801 B2 | 3/2012 | Jones | |
| 8,551,510 B2 | 10/2013 | Bedoukian | |
| 2009/0018192 A1 | 1/2009 | Zhang et al. | |
| 2010/0144888 A1* | 6/2010 | Bessette | A01N 31/04 514/690 |
| 2010/0227010 A1* | 9/2010 | Jones | A01N 37/02 424/747 |
| 2012/0046359 A1 | 2/2012 | Bedoukian | |
| 2012/0148653 A1* | 6/2012 | Jones | A01N 37/02 424/411 |

FOREIGN PATENT DOCUMENTS

| | | | |
|---|---|---|---|
| CN | 101801901 A | | 8/2010 |
| DE | 1960430 | * | 12/1969 |
| WO | WO2010/126576 | * | 11/2010 |
| WO | WO2010126576 | * | 11/2010 |

OTHER PUBLICATIONS 430 translated 1969.*
Fang et al. (Insecticidal Activity of Essential Oil of *Carum carvi* Fruits from China and Its Main Components against Two Grain Storage Insects, Molecules 2010, 15, 9391-9402).*
International Search Report dated Jun. 28, 2013 from PCT/US2013/000119, 3 pages.
Written Opinion dated Jun. 28, 2013 from PCT/US2013/000119, 8 pages.
IPRP dated Nov. 13, 2014 from corresponding PCT Application No. PCT/US2013/000119, 5 pages.
Chinese Office Action dated Aug. 31, 2015 from corresponding Chinese Application No. 201380022681.5, 13 pages.
European Search Report dated Oct. 28, 2015 from corresponding European Patent Application No. 13785292.7, 6 pages.

* cited by examiner

*Primary Examiner* — Yevegeny Valenrod
*Assistant Examiner* — Blaine G Doletski
(74) *Attorney, Agent, or Firm* — Ohlandt, Greeley, Ruggiero & Perle, L.L.P.

(57) ABSTRACT

Killing of bed bugs is accomplished by bringing the bed bugs into contact with a toxic amount of at least one of the compounds of the structure (I)

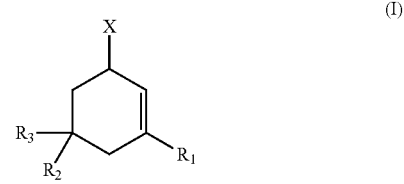

(I)

wherein
X is —OH, =O, or —O(O)CR, wherein R is selected from H and a branched or straight chain, saturated or unsaturated hydrocarbyl group with zero to three double bonds and from 1 to 11 carbon atoms;
$R_1$ is H or $CH_3$;
$R_2$ is H or $CH_3$;
$R_3$ is H or a branched or straight chain, saturated or unsaturated hydrocarbyl group with zero to three double bonds and from 1 to 11 carbon atoms; and
wherein the compounds of structure (I) contain from 6 to 20 total carbon atoms in the compounds.

9 Claims, No Drawings

KILLING OF BED BUGS

FIELD OF THE INVENTION

This invention relates to compounds used as insecticidal agents to kill bed bugs.

BACKGROUND TO THE INVENTION

Recent data suggests bedbug infestations (*Cimex* species) of human domiciles are on the rise. At least 92 species of bed bugs have been identified globally, of which at least 16 species are in the North American continent. Generally, bed bugs are parasitic pests with its hosts including humans and various domesticated animals. It is believed that bedbug infestations are becoming more problematic now at least in part because long acting, residual insecticides are no longer being used to keep bedbug populations in check. In addition, increased international travel and insecticide resistance have made bedbug infestations spread and made control with insecticides very difficult. In terms of scale, such infestations are of particular concern for hoteliers, cruise ships, trains, daycare facilities, and the like because of the business reputation risk posed by bad press or bad reviews. Other problematic areas tend to include nursing homes, barracks, dorms, hospitals, and various other forms of high density housing. Nonetheless, single family homes can likewise be impacted adversely.

Bed bugs feed on human blood. Thus, bed bugs are not merely unsightly, they leave ugly skin markings. However problematic this is for residential bedrooms, it is an even more serious problem for motels and the like. With respect to such commercial bedrooms there is more opportunity for external infection sources to bring bed bugs to the site, and should there be an unknown infestation which causes biting of customers before it is dealt with, there is a severe risk of customer dissatisfaction and adverse publicity, likely leading to a long term significant reputation loss.

There have been attempts to control bedbug infestation through applications of insecticidal chemicals to infected areas and materials (especially mattresses). This approach has some drawbacks. For example, it can expose those using a treated area or mattress too soon after application to odor or other undesired characteristics of the pesticidal chemical. Further, unless the chemicals are used regularly, without regard to whether an infestation is known to already exist (a procedure which will significantly increase costs), those sleeping in an infected area can be bitten before one knows to begin treatment.

Another reason for the increase in bed bugs is that pest control services more often nowadays use low toxicity gel-based pesticides for control of cockroaches, the most common pest in structures, instead of residual sprays. When residual sprays meant to kill other insects were commonly being used, they resulted in a collateral insecticidal effect on potential bedbug infestations. The gel-based insecticides primarily used nowadays do not have any effect on bed bugs, as they are incapable of feeding on these baits. One of the most significant problems in controlling bed bugs is the loss of the ability to use organophosphate pesticides which were very effective, followed by widespread resistance to the use of pyrethroid pesticides which replaced them.

There is, therefore, a need for insecticides that are safe for humans, animals and the environment that can be used to kill bed bugs and for safe and effective means to employ such chemicals.

SUMMARY OF THE INVENTION

In accordance with this invention, killing of bed bugs is obtained by contact of the bed bugs with a toxic amount of at least one of the compounds of the structure (I)

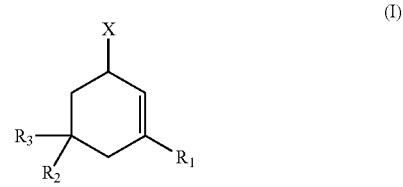

wherein

X is selected from —OH, =O, —O(O)CR, where R is selected from H and a branched or straight chain, saturated or unsaturated hydrocarbyl group with zero to three double bonds and from 1 to 11 carbon atoms;

$R_1$ is selected from H, $CH_3$;

$R_2$ is selected from H, $CH_3$;

$R_3$ is selected from H and a branched or straight chain, saturated or unsaturated hydrocarbyl group with zero to three double bonds and from 1 to 11 carbon atoms, and wherein the compounds of structure (I) contain from 6 to 20 total carbon atoms in the compounds. The invention also includes optical isomers, diastereomers and enantiomers of the compounds of structure (I). Thus, at all stereocenters where stereochemistry is not explicitly defined, all possible epimers are envisioned.

Bed bugs may be killed by bringing the bed bugs into contact with formulations containing at least one compound selected from Structure I as described above. The compounds may be present in any of their isomeric or enantiomeric forms or as mixtures of their isomers or enantiomers.

Further aspects of this invention relate to the use of such formulations in various methods for the killing of bed bugs. Among the various methods in which the formulations of this invention may be employed are (1) injecting or spraying the formulations into or onto a mattress, either directly or in combination with other ingredients or solvents, (2) placing the formulations on an absorbent material and placing the absorbent material in a sachet and placing the sachet containing the formulation into a locus such as, including but not limited to, a mattress, hamper, suitcase, clothing bag, linen storage closet or any other enclosure where bed bugs may be present, (3) preparing "dryer sheets" containing the formulations for placement in a locus such as, including but not limited to, a mattress, suitcase, clothing bag, hamper, clothing bag, linen storage closet, or any other enclosure where bed bugs are likely to be present, or in a pile of clean or soiled laundry, (4) placing the formulation into detergent or fabric softener compositions for killing of bed bugs during use of these compositions in cleaning clothes and sprays or in carpet or floor cleaner products and the like to treat carpets and furniture, (5) spraying a formulation containing the compounds of structure (I) with or without a co-formulant on surfaces, luggage, furniture, into crevices, or behind fixtures and (6) topical application of the formulation intended for use with humans or animals, such as in the form of, including but not limited to, a lotion, wipes, powder, spray or shampoo.

DETAILED DESCRIPTION OF THE INVENTION

Killing of bed bugs is obtained by contact of the bed bugs with a toxic amount of at least one of the compounds of the structure (I)

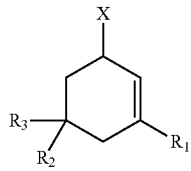

(I)

wherein

X is selected from —OH, =O, —O(O)CR, wherein R is selected from H and a branched or straight chain, saturated or unsaturated hydrocarbyl group with zero to three double bonds and from 1 to 11 carbon atoms;

$R_1$ is selected from H, $CH_3$;

$R_2$ is selected from H, $CH_3$;

$R_3$ is selected from H and a branched or straight chain, saturated or unsaturated hydrocarbyl group with zero to three double bonds and from 1 to 11 carbon atoms and wherein the compounds of structure (I) contain from 6 to 20 total carbon atoms in the compounds. The invention also includes optical isomers, diastereomers and enantiomers of the compounds of structure (I). Thus, at all stereocenters where stereochemistry is not explicitly defined, all possible epimers are envisioned.

Representative examples of compounds of structure (I) include, but are not limited to:

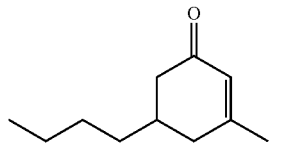

2-Cyclohexen-1-one, 3-methyl-5-propyl-
Chemical Formula: $C_{10}H_{16}O$
Molecular Weight: 152.23

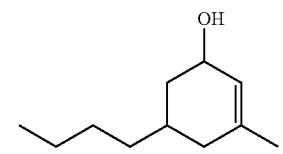

Chemical Formula: C10H18O
Molecular Weight: 154.25
3-methyl-5-propyl-2-cyclohexen-1-ol

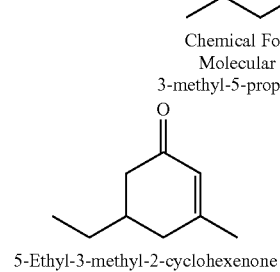

5-Ethyl-3-methyl-2-cyclohexenone
Chemical Formula: $C_9H_{14}O$
Molecular Weight: 138.21

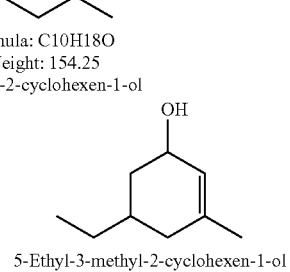

5-Ethyl-3-methyl-2-cyclohexen-1-ol
Chemical Formula: $C_9H_{16}O$
Molecular Weight: 140.22

-continued

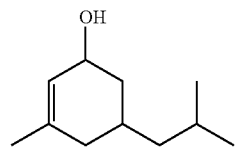

5-Butyl-3-methyl-2-cyclohexenone
Chemical Formula: $C_{11}H_{18}O$
Molecular Weight: 166.26

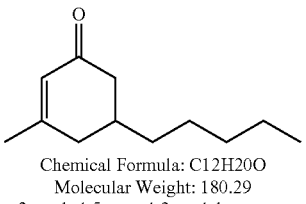

5-Butyl-3-methyl-2-cyclohexen-1-ol
Chemical Formula: $C_{11}H_{20}O$
Molecular Weight: 168.28

Chemical Formula: C11H20O
Molecular Weight: 168.28
3-methyl-5-isobutyl-2-cyclohexen-1-ol

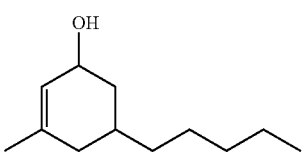

Chemical Formula: C12H20O
Molecular Weight: 180.29
3-methyl-5-pentyl-2-cyclohexenone 3-methyl-5-pentyl-2-cyclohexen-1-ol
Chemical Formula: C12H22O
Molecular Weight: 182.30

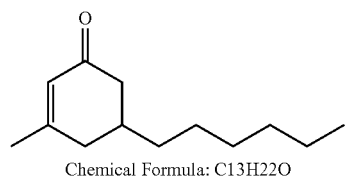

Chemical Formula: C13H22O
Molecular Weight: 194.31
3-methyl-5-hexyl-2-cyclohexenone

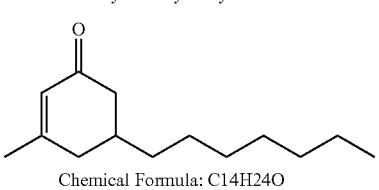

Chemical Formula: C14H24O
Molecular Weight: 208.34
3-methyl-5-heptyl-2-cyclohexenone -continued

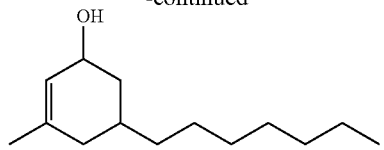

3-methyl-5-heptyl-2-cyclohexen-1-ol
Chemical Formula: C14H26O
Molecular Weight: 210.36

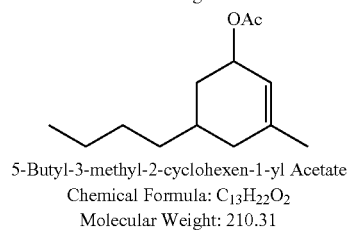

5-Butyl-3-methyl-2-cyclohexen-1-yl Acetate
Chemical Formula: $C_{13}H_{22}O_2$
Molecular Weight: 210.31

A group of especially preferred compounds of structure (I) for the purpose of vapor toxicity is 3-methyl-5-propyl-cyclohexen-1-one, 3-methyl-5-propyl-cyclohexen-1-ol and 3-methyl-5-ethyl-cyclohexen-1-one.

A group of especially preferred compounds of structure (I) for the purpose of contact toxicity is 3-methyl-5-butyl-cyclohexen-1-one, 3-methyl-5-pentylcyclohexen-1-one, and 3-methyl-5-heptylcyclohexen-1-one.

The toxic amount of the compounds of structure (I) to kill bed bugs will be dependent upon the compound employed and the manner in which it is employed and will be readily determined by the user. In general the toxic amount will be in an amount of from about 1% to about 10% by weight of the compound(s) of structure (I) in a formulation.

Toxicity of compounds of structure (I) was determined by forced exposure testing under the following protocol. Five filter paper circles were laid on a flat surface and treated with the test compounds. Five replicates of five bed bugs were released onto each of the treated paper circles. Petri dish bottoms with circular openings were placed over the treated paper circles and served as the exposure arenas. The sides of the Petri dish bottoms were also painted with Fluon to prevent the bed bugs from climbing the sides. The bed bugs were thus confined to the treated paper circles for the duration of the test. Observations were made for mortality of the bed bugs at 24 hours. The bed bug mortality percentage is reported in Table 1.

TABLE 1

| Compound, diluted 5% in acetone | Mortality @ 24 hours |
|---|---|
| 3-Methyl-5-propyl-2-cyclohexenone | 100% |
| 3-Methyl-5-propyl-2-cyclohexenol | 60% |
| 3-Methyl-5-Ethyl-2-Cyclohexenone | 78% |
| 3-Methyl-5-Isobutyl-2-cyclohexenol | 10% |
| 3-Methyl-5-Butyl-2-Cyclohexen-1-one | 50% |

The bed bug toxicant compounds of this invention may be blended with other active repellents or toxicants including, but not limited to, N,N-Diethyl-m-toluamide (DEET®) and p-Menthane-3,8-diol (PMD).

While the invention has been described herein with reference to the specific embodiments thereof, it will be appreciated that changes, modifications and variations can be made without departing from the scope of the inventive concept disclosed herein, and it is intended to embrace all such changes, modification and variations that fall with the scope of the appended claims.

I claim:

1. A method for killing bed bugs, the method comprising contacting the bed bugs with a toxic amount of at least one of the compounds of the structure (I)

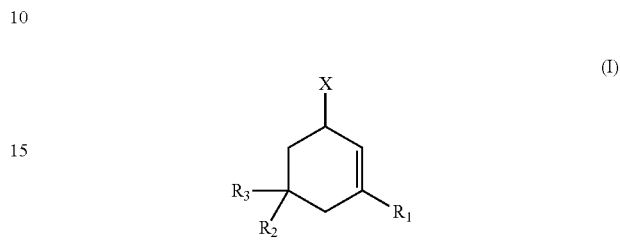

wherein

X is selected from —OH, =O, —O(O)CR, wherein R is selected from H and a branched or straight chain, saturated or unsaturated hydrocarbyl group with zero to three double bonds and from 1 to 11 carbon atoms;

$R_1$ is selected from H, $CH_3$;

$R_2$ is selected from H;

$R_3$ is selected from H and a branched or straight chain, saturated or unsaturated hydrocarbyl group with zero to three double bonds and from 1 to 11 carbon atoms; and wherein the compounds of structure (I) contain from 6 to 20 total carbon atoms in the compounds.

2. The method according to claim 1 wherein the at least one compound of structure (I) is selected from the group consisting of:

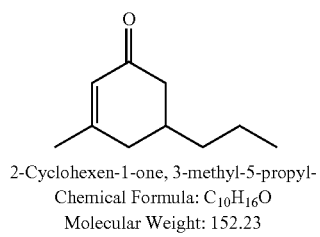

2-Cyclohexen-1-one, 3-methyl-5-propyl-
Chemical Formula: $C_{10}H_{16}O$
Molecular Weight: 152.23

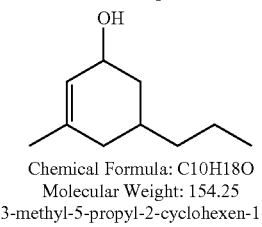

Chemical Formula: C10H18O
Molecular Weight: 154.25
3-methyl-5-propyl-2-cyclohexen-1-ol

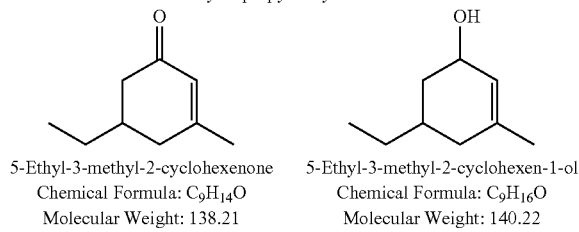

5-Ethyl-3-methyl-2-cyclohexenone
Chemical Formula: $C_9H_{14}O$
Molecular Weight: 138.21

5-Ethyl-3-methyl-2-cyclohexen-1-ol
Chemical Formula: $C_9H_{16}O$
Molecular Weight: 140.22

-continued

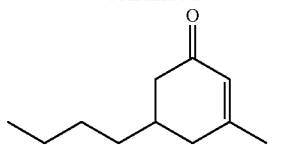

5-Butyl-3-methyl-2-cyclohexenone
Chemical Formula: $C_{11}H_{18}O$
Molecular Weight: 166.26

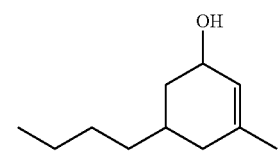

5-Butyl-3-methyl-2-cyclohexen-1-ol
Chemical Formula: $C_{11}H_{20}O$
Molecular Weight: 168.28

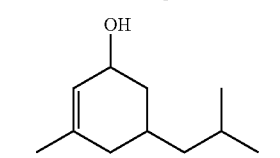

Chemical Formula: C11H20O
Molecular Weight: 168.28
3-methyl-5-isobutyl-2-cyclohexen-1-ol

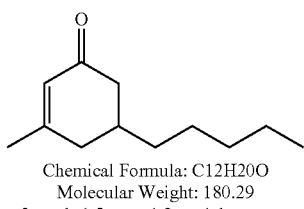

Chemical Formula: C12H20O
Molecular Weight: 180.29
3-methyl-5-pentyl-2-cyclohexenone

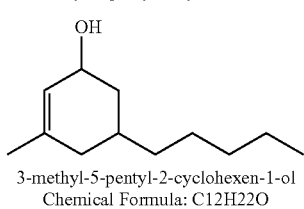

3-methyl-5-pentyl-2-cyclohexen-1-ol
Chemical Formula: C12H22O
Molecular Weight: 182.30

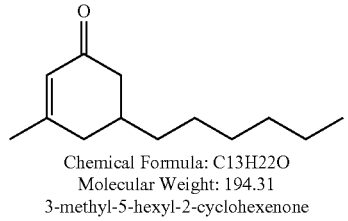

Chemical Formula: C13H22O
Molecular Weight: 194.31
3-methyl-5-hexyl-2-cyclohexenone -continued

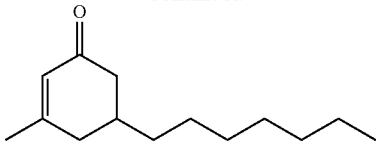

Chemical Formula: C14H24O
Molecular Weight: 208.34
3-methyl-5-heptyl-2-cyclohexenone

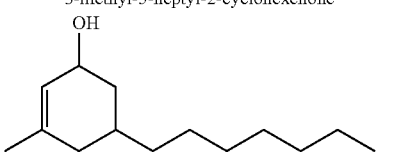

and 3-methyl-5-heptyl-2-cyclohexen-1-ol
Chemical Formula: C14H26O
Molecular Weight: 210.36

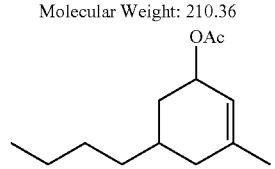

5-Butyl-3-methyl-2-cyclohexen-1-yl Acetate
Chemical Formula: $C_{13}H_{22}O_2$
Molecular Weight: 210.31.

3. The method according to claim 1 wherein the bed bugs are brought into contact with at least two compounds of structure (I).

4. The method according to claim 1 wherein at least one compound of structure (I) is applied to surface of or impregnated into clothing or fabric.

5. The method according to claim 1 wherein at least one compound of structure (I) is applied to detergents, fabric softeners or dryer sheets.

6. The method according to claim 1 wherein at least one compound of structure (I) is applied as a topical toxicant formulation in the form of a lotion, wipe, powder, spray or shampoo.

7. The method according to claim 1 wherein at least one compound of structure (I) is applied to furniture, building supplies, electronic devices, cargo or storage areas.

8. The method according to claim 1 wherein at least one compound of structure (I) is selected from the group consisting of 3-methyl-5-propyl-2-cyclohexen-1-one, 3-methyl-5-propyl-2-cyclohexen-1-ol and 5-ethyl-3-methyl-2-cyclohexenone for vapor toxicity.

9. The method according to claim 1 wherein at least one compound of structure (I) is selected from the group 5-butyl-3-methyl-2-cyclohexenone, 3-methyl-5-pentyl-2-cyclohexen-1-one, 3-methyl-5-hexyl-2-cyclohexenone and 3-methyl-5-heptyl-2-cyclohexen-1-one for contact toxicity.

* * * * *